United States Patent
Roberts et al.

(10) Patent No.: US 6,632,168 B2
(45) Date of Patent: Oct. 14, 2003

(54) MAGNETIC THERAPEUTIC DEVICE AND METHOD OF USE

(75) Inventors: Donald L. Roberts, Escondido, CA (US); Arthur J. Devine, Escondido, CA (US); Larry R. Haase, Escondido, CA (US)

(73) Assignee: Advanced Recording Technologies, Escondido, CA (US)

( * ) Notice: Subject to any disclaimer, the term of this patent is extended or adjusted under 35 U.S.C. 154(b) by 0 days.

(21) Appl. No.: 09/887,219

(22) Filed: Jun. 20, 2001

(65) Prior Publication Data

US 2002/0198433 A1 Dec. 26, 2002

Related U.S. Application Data

(60) Provisional application No. 60/276,940, filed on Mar. 13, 2001.

(51) Int. Cl.$^7$ ................................................ A61N 21/00

(52) U.S. Cl. .............................. 600/9; 600/15; 63/900

(58) Field of Search ................................ 600/9, 15, 12; 63/900, 29.2, 20; 24/66.1, 303; 2/279

(56) References Cited

U.S. PATENT DOCUMENTS

| | | | |
|---|---|---|---|
| 5,186,373 A | * 2/1993 | Taylor | 156/213 |
| 5,813,971 A | * 9/1998 | Broderick | 600/15 |
| 5,950,239 A | * 9/1999 | Lopez | 2/115 |
| 5,974,634 A | * 11/1999 | Eisenpresser | 24/303 |
| 6,006,363 A | * 12/1999 | Karlin | 2/228 |
| 6,245,006 B1 | * 6/2001 | Olson | 600/15 |
| 6,282,760 B1 | * 9/2001 | Mars | 24/303 |
| 6,344,021 B1 | * 2/2002 | Juster et al. | 600/15 |

OTHER PUBLICATIONS

Author Unknown, Abstract—"Magnetic Bio–Stimulation In Painful Diabetic Peripheral Neuropathy: A Novel Intervention—A Randomized, Double–Placebo Crossover Study," *AJPM*9(1);8–17(1999).
Author Unknown, "The History of Magnetic Therapy."
Assenmacher, Mario, "High Gradient Magnetic Separation in Biomedical Applications, " http://www.medico.dk/mario.htm. (Printed May 5, 2001).
Brown, CS, "Effect of Magnets on Chronic Pelvic Pain," *Obstet. Gynecol.*,Apr. 1, 2000:95(4 Supp):S29.
Israeli, E., "Collagen Development In Tissue Cultures In Vitro Under Static Magnetic Fields," *Isr. J. Med. Sci.*, Mar.; 7(3):465–468.
Vallbona, C., "Response Of Pain To Static Magnetic Fields In Postpolio Patients: A Double–Blind Pilot Study," *Arch Phys Med Rehabil*, Nov;78(11)1200–3.
Zimmerman, Dr. John, "The Two Different Definitions of the North and South Magnetic Poles, " *Journal of the Bio–Electro–Magnetic Institute*, 3(2):14 (1991).

* cited by examiner

*Primary Examiner*—Gregory Huson
*Assistant Examiner*—Amanda Flynn
(74) *Attorney, Agent, or Firm*—Procopia, Cory, Hargreaves & Savitch, LLP

(57) ABSTRACT

A magnetic therapeutic device for application to a target pain or injury area under a user's skin includes a plurality of hook-like members for attaching to an inner surface of a user's clothing adjacent the target pain or injury. In an embodiment, the device further comprises a plastic member including a smooth surface for contacting the user's skin adjacent the target pain or injury area, a magnet sandwiched between the hook-like members and the plastic member for generating a magnetic field in the target pain or injury area under the user's skin, and a keeper for placing outside a user's clothing. In an embodiment, the device is held in place by the attractive force of the magnet to pinch the clothing between the magnet and the keeper.

27 Claims, 2 Drawing Sheets

MAGNETIC THERAPEUTIC DEVICE AND METHOD OF USE

This application claims benefit of provisional application Ser. No. 60/276,940 filed Mar. 13, 2001.

FIELD OF THE INVENTION

The present invention is in the field of magnetic devices used for therapeutic purposes.

BACKGROUND OF THE INVENTION

It has been believed for thousands of years that magnets assist in pain relief. More recent scientific studies have helped to validate this belief. In a freely suspended bar magnet, the end of the magnet that points generally in a north direction is designated as the biomagnetic south pole (−) and the end of the magnet that points generally in a south direction is called the biomagnetic north pole (+). Dr. Robert O. Becker discovered that initially any injury registers electromagnetic positive (+), regardless of whether the injury is a cut, bruise, or broken bone. In the case of a broken bone, the broken area registers electromagnetic positive for about three hours and then registers electromagnetic negative. Dr. Becker found that during the healing process, the body concentrates electromagnetic negative energy at the site of injury and it is only when electromagnetic negative energy is present that healing can occur. C. S. Brown, et. al. discovered in their research on Chronic Pelvic Pain that a significant reduction of pain was related to duration of exposure to static magnets placed on trigger points in the pelvic region. C. Vallbona, et. al. found that the application of static magnetic fields over a pain trigger point results in significant and prompt pain relief of pain in post polio subjects. M. Weintraub determined that there was a 60% statistical reduction of pain and 100% elimination of burning foot syndrome in diabetic patients who used static magnetics. According to E. Israeli, et. al., "From the experiments conducted so far, mostly in the 10,000 gauss range, it seems as though the magnetic field causes an intensification of the entire tissue, a thickening of the collagen fibers and as a result of this, an over-all increase in the collagen density." In the past, a magnet was applied to a targeted pain area in the body by wrapping the magnet with a gauze bandage, tape, etc. over the targeted area. Not only can this be unsightly, but it is cumbersome, it may require the assistance of another person, and it requires a special bandage, tape, etc.

According to E. Israeli, et. al., "From the experiments conducted so far, mostly in the 10,000 gauss range, it seems as though the magnetic field causes an intensification of the entire tissue, a thickening of the collagen fibers and as a result of this, an over-all increase in the collagen density." In the past, a magnet was applied to a targeted pain area in the body by wrapping the magnet with a gauze bandage, tape, etc. over the targeted area. Not only can this be unsightly, but it is cumbersome, it may require the assistance of another person, and it requires special a special bandage, tape, etc.

Therefore, a need exists for a simple, inexpensive, easy-to-apply, more effective magnetic therapeutic device and method of use.

SUMMARY OF THE INVENTION

An aspect of the invention involves a magnetic therapeutic device for application to a target pain or injury area under a user's skin. The magnetic therapeutic device includes a plurality of hook-like members adapted to be attached to an inner surface of a user's clothing adjacent the target pain or injury, a plastic member including a smooth surface adapted to contact the user's skin adjacent the target pain or injury area, a magnet sandwiched between the hook-like members and the plastic member and adapted to generate a magnetic field in the target pain or injury area under the user's skin, and a keeper adapted to be placed outside a user's clothing and held in place by the attractive force of the magnet to pinch the clothing between the magnet and the keeper to hold the device in place.

Another aspect of the invention involves a magnetic therapeutic device for application to a target pain or injury area under a user's skin. The magnetic therapeutic device includes a magnetic therapeutic patch including a clothing contact surface adapted to contact an inner surface of a user's clothing adjacent the target pain or injury area under a user's skin, a skin contact surface adapted to contact the user's skin adjacent the target pain or injury area, a magnet adapted to generate a magnetic field in the target pain or injury area under the user's skin; and a keeper adapted to be placed outside the user's clothing and held in place by the attractive force of the magnet to pinch the clothing between the magnet and the keeper to hold the device in place.

A further aspect of the invention involves a magnetic therapeutic device for application to a target pain or injury area under a user's skin. The magnetic therapeutic device includes a clothing contact surface adapted to contact an inner surface of a user's clothing adjacent the target pain or injury area under a user's skin, a skin contact surface adapted to contact the user's skin adjacent the target pain or injury area, a magnet adapted to generate a magnetic field in the target pain or injury area under the user's skin, and means for holding the device in place and increasing magnetic field penetration under the skin.

A further aspect of the invention involves a method of treating a target pain or injury area under a user's skin using a magnetic therapeutic device. The method includes providing a magnet adapted to generate a magnetic field in the target pain or injury area; providing a keeper adapted to be placed outside a user's clothing and held in place by the attractive force of the magnet to pinch the clothing between the magnet and the keeper to hold the device in place; placing the magnet under the user's clothing, adjacent the target pain or injury area; and placing the keeper outside the user's clothing adjacent the magnet so that the magnet and keeper are held in place adjacent the target pain or injury area by the attractive force of the magnet and the keeper pinching the clothing therebetween.

A still further aspect of the invention involves a method of treating a target pain or injury area under a user's skin using a magnetic therapeutic device. The method includes binding a magnetically attractable substance with one or more therapeutic elements to form one or more magnetically attractable therapeutic elements; providing a magnet adapted to generate a magnetic field; locating the magnet adjacent the target pain or injury area so as to generate a magnetic field under the user's skin in the target pain or injury area; and drawing the one or more magnetically attractable therapeutic elements to the target pain or injury area with the magnetic field generated in the target pain or injury area under the user's skin.

These and further objects and advantages will be apparent to those skilled in the art in connection with the drawing and the detailed description of the preferred embodiment set forth below.

DETAILED DESCRIPTION OF THE PREFERRED EMBODIMENT

Figure 1:
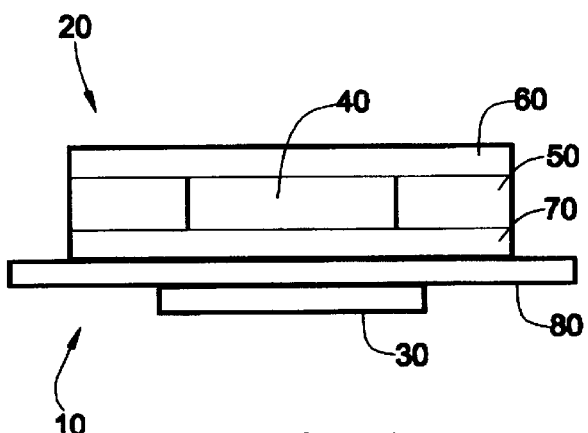
FIG. 1 is a cross-sectional view of an embodiment of the magnetic therapeutic device.
Figure 2:
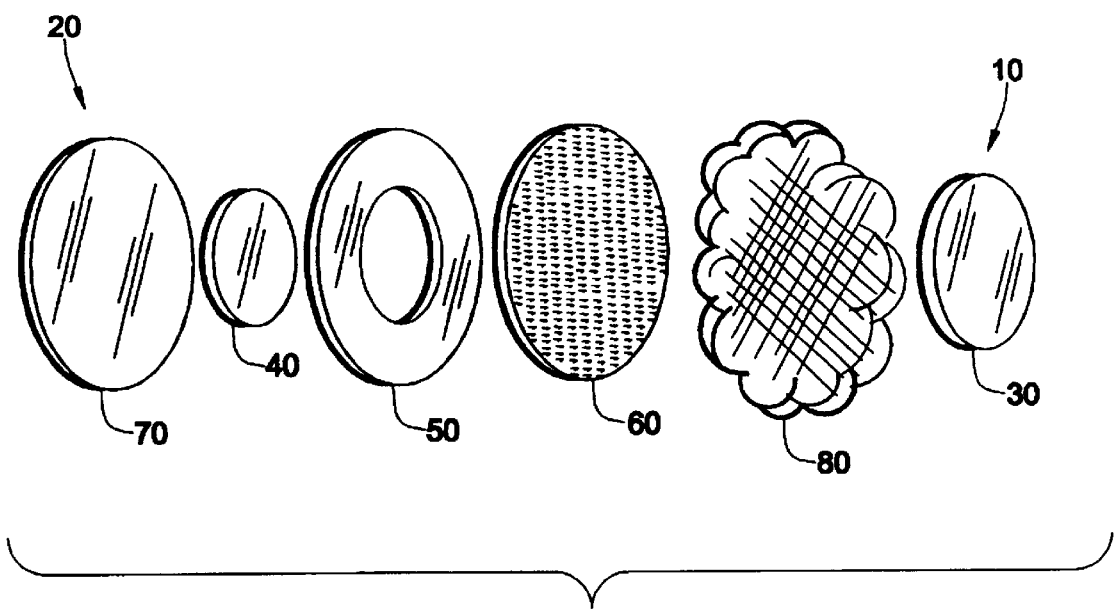
FIG. 2 is an exploded perspective view of the elements of the embodiment of the magnetic therapeutic device illustrated in FIG. 1.

With reference to FIGS. 1 and 2, an embodiment of a magnetic therapeutic device 10 will now be described. The magnetic therapeutic device 10 generally includes a flexible, washable, durable, long-lasting, reusable magnetic patch 20 and a ferro-magnetic disc or keeper 30.

In the illustrated embodiment, the magnetic patch 20 includes a nickel-sized Neodymium Iron Boron magnet 40 mounted within a donut-shaped, plastic foam ring 50 that is sandwiched between a Velcro®hook disc 60 and a very thin plastic disc or membrane 70. Each of these elements will be described in turn below.

In the embodiment shown, the magnet 40 is a disc-shaped, ¾ in. diameter, corrosion-resistant, nickel-plated, Neodymium Iron Boron rare-earth magnet. The magnet 40 generates a significant magnetic field (about $B_r$ 12,650 gauss) that penetrates beyond about one inch below the skin surface when placed at the skin surface. The strength of the magnet 40 is believed to increase collagen fiber thickness and density, and, as described further below, may be used to draw magnetically attractable therapeutic elements (e.g., stem cells) to the target pain or injury area. Collagen is necessary for the healing of joints and muscle tissue. Concentrating therapeutic elements such as stem cells at the target area are believed to accelerate the healing process in this area. The magnet 40 may be made of magnetic materials other than a Neodymium Iron Boron rare-earth magnet. Further, the magnet 40 may have a configuration and/or dimensions other than that shown and described herein.

The donut-shaped, plastic foam ring 50 includes an inner hole with a diameter of about three-quarter in. and an outer diameter of about two in. The magnet 40 is received within the inner hole of the ring 50 and the two components are affixed to each other with an appropriate adhesive. The thickness of the plastic foam ring 50 and the magnet 40 are approximately the same in order to maximize comfort and provide uniform surfaces that press against the body and the clothing being worn. It will be readily apparent to those skilled in the art that ring 50 may be made of a different material and/or have different dimensions than that shown and described herein. Further, in alternative embodiments, the ring 50 may not exist; the ring 50 could be replaced with a magnet having the same or a different diameter.

The Velcro®hook disc 60 includes a plurality of hook-like members extending from one surface of the two in. diameter disc 60. The opposite surface is adhered to the plastic foam ring 50 and/or magnet 40 using any well-known adhesive or with a stick backing. The hook-like members are part of a clothing contact surface and adhere, catch, or hook the patch 20 to an inner surface of certain types of clothing 80 (e.g., fabric, garment, apparel, bandage, tape, etc.) The clothing 80 may include one or more layers of clothing or one or more layers of multiple layers of clothing. Clothing includes anything worn by a person that covers or partially covers the user's skin. The rough attachment surface provided by the hook-like members also helps to prevent slippage of the patch 20 relative to the clothing 80. In alternative embodiments, the disc 60 may have an alternative configuration, may have alternative dimensions, and/or may be made of a material other than a Velcro®hook material. Further, in another embodiment, the disc 60 may not exist; the disc 60 could be replaced with the ring 50 and magnet 40, or just a magnet 40 (one surface of the magnet 40 would form the clothing contact surface and another surface of the magnet would form a skin contact surface).

The plastic disc or membrane 70 may be made of a non-porous polyolifin material resistant to breakdown and degradation. The membrane 70 is made very thin so that the magnet 40 will be as close as possible to a person's skin without touching the skin. The proximity of the magnet 40 to the skin surface is paramount in allowing magnetic flux to penetrate the skin so as to promote pain relief from injury, disease, etc. in the target area. In the embodiment shown, the disc 70 includes a two in. diameter and may be made of any suitable plastic or other material. The magnet 40 and the ring 50 are affixed to one side of the plastic disc 70 with an appropriate adhesive. In alternative embodiments, the membrane 70 may have an alternative configuration, may have alternative dimensions, and/or may be made of a different material. Further, in another embodiment, the membrane 70 may not exist; the membrane 70 could be replaced with the ring 50 and magnet 40, or just a magnet of a predetermined diameter.

The keeper 30 is placed outside the clothing 80 and held in place by the attractive force of the magnet 40 to aid in preventing the magnet 40 from slipping out of place. The attractive force pinches the clothing 80 between the magnet 40 and the keeper 30, preventing slippage. The keeper 30 may include a rough surface to provide friction that assists in preventing the magnet 40 from slipping over the clothing 80, out of place over the target area. The keeper 30 may eliminate the need for an unsightly wrap brace, elastic bandage, tape, etc. to hold the magnetic therapeutic patch in place over the target pain/injury area. The keeper 30 may be made of a ferromagnetic material to enhance the strength of the magnetic field by approximately 30–100% compared to the magnet 40 alone. The keeper 30 may shorten the lines of flux by approximately a factor of 2 compared to the magnet 40 alone. In an alternative embodiment, to further enhance the strength the keeper 30 is made of a magnetic material (e.g., neodymium magnet) instead of a ferromagnetic material or is made of a magnetic material and a ferromagnetic material. For example, the keeper 30 may include a small magnet attached to ferromagnetic material.

The magnetic therapeutic device 10 is believed to assist in pain relief and healing of a variety of complications such as, but not by way of limitation, sports injuries, ligament sprains, muscle strains, carpal tunnel syndrome, joint injuries, back pain, and bone damage.

Figure 3:
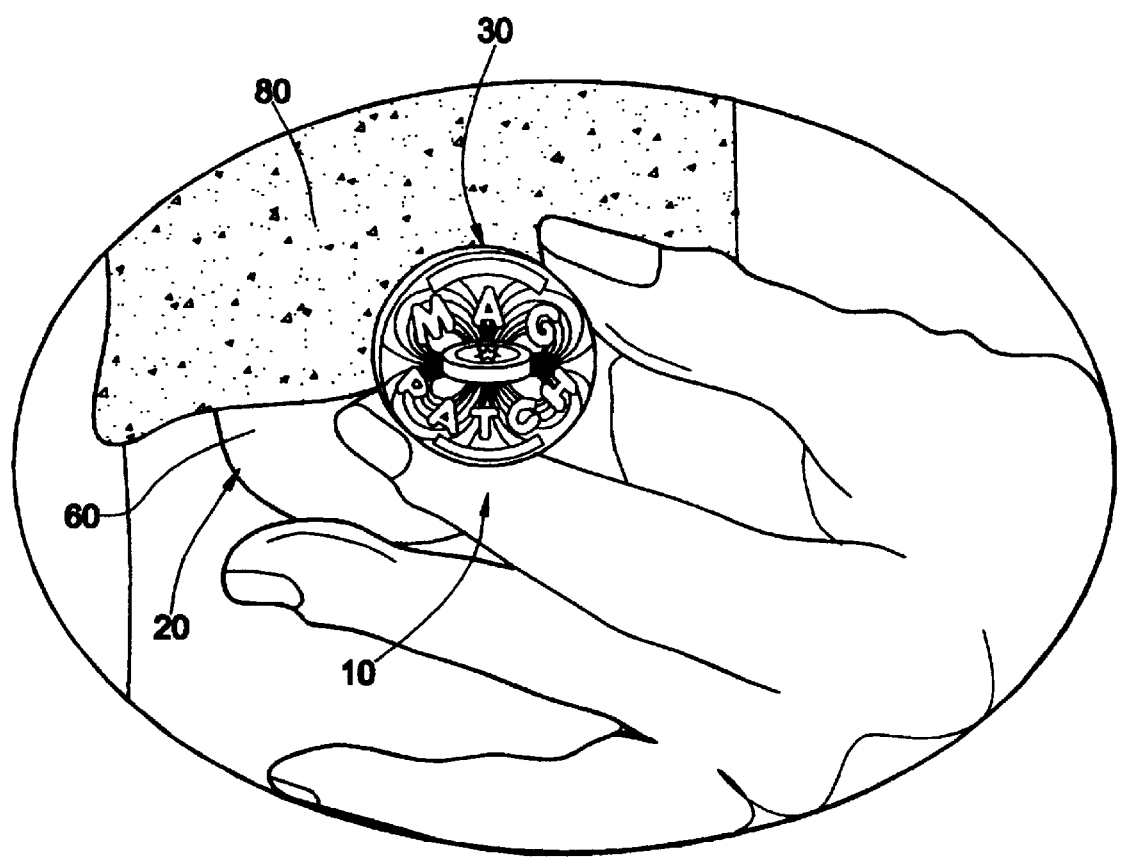
FIG. 3 is a perspective view of an embodiment of the magnetic therapeutic device being applied to a user's clothing over a target pain or injury area.

With reference additionally to FIG. 3, the magnetic therapeutic device 10 will now be described in use. The magnetic therapeutic device 10 is conveniently held in place against the skin to allow strong magnetic flux from the magnet 40 to penetrate the skin in order to provided pain relief from injury or disease in the target area. This is done by first placing the magnetic therapeutic patch 20 under a layer of clothing 80 with the smooth side or plastic disc 70 facedown, preferably on the skin over the target pain or injury area. The patch 20 does not have to be against the user's skin. For example, the patch 20 may be located between layers of clothing. Thus, under the user's clothing means that the patch 20 is under all layers of a user's clothing or under one or more layers of multiple layers of the user's clothing. Next, the hook-like fasteners of the Velcro hook disc 60 are hooked or affixed to the inner surface of the clothing 80, if possible. The patch 20 is then secured in place over the target area by placing the keeper 30 on the outside of the clothing 80, over the patch 20. The outside of the user's clothing 80 does not have to be directly against an outermost surface of the clothing 80. For example, the patch 20 may be located between layers of clothing, i.e. outside one or more layers, but inside one or more additional layers. Thus, outside the user's clothing means that the patch 20 is outside all layers of a user's clothing or outside one or more layers of multiple layers of the user's clothing. The attractive force of the magnet 40 attracts the keeper 30 to the patch 20, causing the clothing 80 to be pinched between the magnet 40 and the keeper 30, preventing slippage. A rough surface on the keeper 30 may assist in preventing the keeper 30 and the magnet 40 from slipping over the clothing 80. The keeper 30 holds the magnetic therapeutic patch 20 in place over the target pain/injury area and strengthens the magnetic field generated by the device 10.

In an alternative embodiment, a magnetically attractable substance may be added to a group of elements to bind with one or more therapeutic elements in the group. Then, using the magnetic therapeutic device 10, a magnetic field may be applied to the target pain/injury area in the manner described above to draw the now magnetically attractable therapeutic elements to the target pain/injury area for therapeutic purposes. For example, but not by way of limitation, a magnetically attractable substance designed to bind with one or more stem cells may be added to a group of cells. A binding agent may be conjugated to small (e.g., 200 nm) superparamagnetic particles (microbeads). The resulting magnetically attractable substance may be added to a group of cells by, for example, injecting the substance into the user's blood stream, joint, body tissue, etc. The magnetically attractable substance may then bind with the therapeutic stem cells. Applying a magnetic field to the target pain/injury area with the magnetic therapeutic device 10 may cause the magnetically attractable stem cells to migrate or concentrate in the target area to promote healing in this area. Although in the example given the therapeutic elements that are magnetically charged and controlled for therapeutic purposes are stem cells, other therapeutic elements (e.g., drugs, other types of cells) may be magnetically charged and controlled in a similar manner. Further, magnetic elements other than the above-described superparamagnetic microbeads may be used to charge the therapeutic elements.

Thus, the magnetic therapeutic device 10 is simple, inexpensive, easy-to-apply, and more effective than magnetic devices used in the past. The magnetic therapeutic device 10 and method are believed to generate a significant magnetic field (greater than about $B_r$ 12,000 gauss) that penetrates beyond about one inch below the skin surface to effectively stimulate enzyme production in the underlying cells and increase collagen fiber thickness and density, which is necessary for the healing of joints and muscle tissue. The device 10 and method may also be used to attract or draw magnetically attractable therapeutic elements (e.g., magnetically charged stem cells) to the target pain or injury area. One or more of these factors is believed to alleviate the pain/injury in the target area.

It will be readily apparent to those skilled in the art that still further changes and modifications in the actual concepts described herein can readily be made without departing from the spirit and scope of the invention as defined by the following claims.

What is claimed is:

1. A magnetic therapeutic device for application to a target pain or injury area under a user's skin, comprising:
    a plurality of hook-like members adapted to be attached to an inner surface of a user's clothing adjacent the target pain or injury area under a user's skin;
    a plastic member including a smooth surface adapted to contact the user's skin adjacent the target pain or injury area;
    a magnet sandwiched between the hook-like members and the plastic member, the magnet adapted to generate a magnetic field in the target pain or injury area under the user's skin; and
    a keeper adapted to be placed outside a user's clothing and held in place by the attractive force of the magnet to pinch the clothing between the magnet and the keeper to hold the device in place.

2. The device of claim 1, wherein the hook-like members are part of a disc, and the plastic member is a plastic disc.

3. The device of claim 1, further including a ring member with a central area, the magnet disposed within the central area of the ring member, the ring member and the central area sandwiched between the hook-like members and the plastic member.

4. The device of claim 3, wherein the ring member is a plastic foam ring with a circular central area, and the magnet is a circular magnet disposed within the circular central area of the plastic foam ring member.

5. The device of claim 1, wherein the magnet generates a magnetic field greater than $B_r$ 12,000 gauss.

6. The device of claim 1, wherein the magnet generates a magnetic field that penetrates beyond about one inch below the skin surface.

7. The device of claim 1, wherein the magnet generates a magnetic field of about $B_r$ 12,650 gauss.

8. The device of claim 1, wherein the magnet is a Neodymium magnet.

9. The device of claim 1, wherein the magnet is a corrosion-resistant, nickel-plated magnet.

10. The device of claim 1, wherein the keeper is made of a magnetic material.

11. The device of claim 1, wherein the keeper is made of a ferromagnetic material.

12. The device of claim 1, wherein the keeper includes a rough friction surface adapted to contact the user's clothing to help hold the device in place.

13. The device of claim 1, wherein the keeper is made of a material that increases magnetic field penetration under the skin.

14. The device of claim 1, wherein the plastic member is made of a non-porous polyolifin material.

15. A magnetic therapeutic device for application to a target pain or injury area under a user's skin comprising a magnetic therapeutic patch including a clothing contact surface having a plurality of hook-like members adapted to contact an inner surface of a user's clothing adjacent the target pain or injury area under a user's skin, a skin contact surface adapted to contact the user's skin adjacent the target pain or injury area, a magnet adapted to generate a magnetic field in the target pain or injury area under the user's skin; and a keeper adapted to be placed outside the user's clothing and held in place by the attractive force of the magnet to pinch the clothing between the magnet and the keeper to hold the device in place.

16. The device of claim 15, wherein the skin contact surface is part of a thin plastic membrane.

17. The device of claim 15, further including a ring member with a central area, the magnet disposed within the central area of the ring member.

18. A method of treating a target pain or injury area under a user's skin using a magnetic therapeutic device, comprising:
- binding a magnetically attractable substance with one or more therapeutic elements to form one or more magnetically attractable therapeutic elements;
- providing a magnet adapted to generate a magnetic field;
- locating the magnet adjacent the target pain or injury area so as to generate a magnetic field under the user's skin in the target pain or injury area;
- drawing the one or more magnetically attractable therapeutic elements to the target pain or injury area with the magnetic field generated in the target pain or injury area under the user's skin.

19. The method of claim 18, wherein the magnet is part of magnetic therapeutic device including the magnet, an attachment surface adapted to be attached to an inner surface of a user's clothing adjacent the target pain or injury area, and a smooth skin contact surface adapted to contact the user's skin adjacent the target pain or injury area.

20. The method of claim 18, wherein the magnet generates a magnetic field that penetrates beyond about one inch below the skin surface.

21. The method of claim 18, wherein the magnet is a Neodymium magnet.

22. The method of claim 18, wherein the magnet generates a magnetic field greater than $B_r$ 12,000 gauss.

23. The method of claim 18, wherein the one or more therapeutic elements are one or more stem cells.

24. The method of claim 18, wherein the magnetically attractable substance includes a binding agent conjugated to small superparamagnetic particles.

25. The method of claim 18, further including introducing the magnetically attractable substance into the user adjacent the target pain or injury area.

26. The method of claim 18, further including introducing the one or more magnetically attractable therapeutic elements into the user adjacent the target pain or injury area.

27. The method of claim 18, further including providing a keeper adapted to be placed outside a user's clothing and held in place by the attractive force of the magnet to pinch the clothing between the magnet and the keeper to hold the device in place; placing the magnet under the user's clothing, adjacent the target pain or injury area; and placing the keeper outside the user's clothing adjacent the magnet so that the magnet and keeper are held in place adjacent the target pain or injury area by the attractive force of the magnet and the keeper pinching the clothing therebetween.

* * * * *